(12) United States Patent
Kim et al.

(10) Patent No.: US 10,278,928 B2
(45) Date of Patent: May 7, 2019

(54) FILM-FORMING PHARMACEUTICAL COMPOSITION FOR WOUND HEALING AND METHOD FOR PREPARING THE SAME

(71) Applicant: DONG-A PHARMACEUTICAL CO., LTD., Seoul (KR)

(72) Inventors: Soon Hoe Kim, Gyeonggi-do (KR); Mi Won Son, Gyeonggi-do (KR); Sun Woo Jang, Seoul (KR); Joon Ho Jun, Gyeonggi-do (KR); Sang Dug Han, Gyeonggi-do (KR); Sung Rak Choi, Incheon (KR); Dae Hwan Kim, Gyeonggi-do (KR); Yong Sung Sohn, Seoul (KR); Yong Sam Kwon, Gyeonggi-do (KR)

(73) Assignee: Dong-A Pharmaceutical Co., Ltd, Seoul (KR)

( * ) Notice: Subject to any disclaimer, the term of this patent is extended or adjusted under 35 U.S.C. 154(b) by 0 days.

(21) Appl. No.: 14/765,318

(22) PCT Filed: Feb. 11, 2014

(86) PCT No.: PCT/KR2014/001103
§ 371 (c)(1),
(2) Date: Jul. 31, 2015

(87) PCT Pub. No.: WO2014/126370
PCT Pub. Date: Aug. 21, 2014

(65) Prior Publication Data
US 2015/0374641 A1    Dec. 31, 2015

(30) Foreign Application Priority Data
Feb. 13, 2013 (KR) ........................ 10-2013-0015400

(51) Int. Cl.
| A61K 9/70 | (2006.01) |
| A61K 9/00 | (2006.01) |
| A61K 31/722 | (2006.01) |
| A61K 47/36 | (2006.01) |
| A61K 31/573 | (2006.01) |
| A61K 31/575 | (2006.01) |
| A61K 31/7036 | (2006.01) |
| A61K 31/567 | (2006.01) |
| A61K 38/12 | (2006.01) |
| A61K 47/12 | (2006.01) |
| A61K 9/06 | (2006.01) |

(52) U.S. Cl.
CPC .......... *A61K 9/7015* (2013.01); *A61K 9/0014* (2013.01); *A61K 9/06* (2013.01); *A61K 31/567* (2013.01); *A61K 31/573* (2013.01); *A61K 31/575* (2013.01); *A61K 31/7036* (2013.01); *A61K 31/722* (2013.01); *A61K 38/12* (2013.01); *A61K 47/12* (2013.01); *A61K 47/36* (2013.01)

(58) Field of Classification Search
CPC ................................. A61K 9/70; A61K 31/722
See application file for complete search history.

(56) References Cited

U.S. PATENT DOCUMENTS

| 4,659,700 | A * | 4/1987 | Jackson .............. A61L 26/0023 514/55 |
| 4,935,241 | A | 6/1990 | Saitoh et al. .................... 424/81 |
| 6,211,250 | B1 | 4/2001 | Tomlinson et al. ........ 514/772.4 |
| 2002/0054910 | A1 * | 5/2002 | Ronchi ................ A61K 9/7015 424/486 |
| 2003/0104020 | A1 * | 6/2003 | Davison ................... A61K 8/02 424/401 |
| 2009/0047331 | A1 * | 2/2009 | Kim ........................ A61L 15/28 424/445 |
| 2012/0040946 | A1 * | 2/2012 | Sulur ................... A61K 9/0014 514/182 |

(Continued)

FOREIGN PATENT DOCUMENTS

| CN | 103006923 B | * | 5/2014 |
| EP | 1 179 352 |  | 2/2002 |

(Continued)

OTHER PUBLICATIONS

English machine translation of CN103006923 B (obltained online dated May 27, 2016).*
U.S. Appl. No. 13/641,867, filed Nov. 21, 2012, U.S. Pat. No. 2013/0085160, dated Apr. 4, 2013.
U.S. Appl. No. 14/003,077, filed Oct. 3, 2013, U.S. Pat. No. 2014/0044817, dated Feb. 13, 2014.
U.S. Appl. No. 14/003,087, filed Oct. 3, 2013, U.S. Pat. No. 2014/0017345, dated Jan. 16, 2014.

(Continued)

*Primary Examiner* — H. Sarah Park
(74) *Attorney, Agent, or Firm* — Dentons US LLP; Stephanie Seidman; Frank J. Miskiel (57) ABSTRACT

The present invention relates to a pharmaceutical composition for forming a film directly on a wound to accelerate wound healing, a use for the same, a treatment method using the same, and a method for preparing the same. The film-forming composition according to the present invention forms a film directly on the wound to increase the adhesion to the wound. The formed thin hydrophilic film protects the wound surface to prevent infection of the wound surface, retains the physiologically active substance useful for wound healing on the wound surface to promote the wound healing, and allow drugs to be continuously delivered to the wound surface. Therefore, the composition according to the present invention has excellent wound healing effect and has excellent usability as it is not absorbed into clothing, bandage, etc., thus effectively replacing conventional gel or ointment formations for delivering physiologically active substances.

17 Claims, 1 Drawing Sheet

(56) References Cited

U.S. PATENT DOCUMENTS

| | | | |
|---|---|---|---|
| 2013/0085160 A1 | 4/2013 | Kim et al. | 514/229 |
| 2013/0296571 A1 | 11/2013 | Son et al. | 546/75 |
| 2013/0317052 A1 | 11/2013 | Son et al. | 514/289 |
| 2014/0017345 A1 | 1/2014 | Kim et al. | 424/725 |
| 2014/0044817 A1 | 2/2014 | Kim et al. | 424/773 |
| 2014/0274943 A1* | 9/2014 | Subramaniam | A61K 9/0014 514/55 |

FOREIGN PATENT DOCUMENTS

| | | |
|---|---|---|
| KR | 1996-0009415 | 7/1996 |
| KR | 10-2002-0066024 | 2/2001 |
| KR | 10-0440239 | 7/2004 |
| KR | 10-2006-0015215 | 2/2006 |
| KR | 10-0551930 | 2/2006 |
| KR | 10-0608192 | 7/2006 |
| KR | 10-0644369 | 11/2006 |
| KR | 10-0748390 | 8/2007 |
| KR | 10-2008-0049797 | 6/2008 |
| KR | 10-0979347 | 8/2010 |
| KR | 10-2011-0027434 | 3/2011 |
| KR | 10-2011-0074116 | 6/2011 |
| KR | 10-2012-0022930 | 3/2012 |
| KR | 10-2012-0023653 | 3/2012 |
| WO | WO 2007/039533 | 4/2007 |

OTHER PUBLICATIONS

Letter/Written Disclosure of the Information Disclosure Statement for the above-referenced application, dated Dec. 14, 2015, 3 pages.
Dong-A Group website, "Pipeline," Copyright 2009 [online][retrieved on Jul. 7, 2013] Retrieved from:<URL:en.donga.co.kr/rnd/rnd03.jsp, 2 pages.
Dong-A Group website, "R&D at Dong-A," Copyright 2009 [online][retrieved on Jul. 7, 2013] Retrieved from:<URL:en.donga.co.kr/rnd/rnd01.jsp , 1 page.
Dong-A Group website, "Research Center," Copyright 2009 [online][retrieved on Jul. 7, 2013] Retrieved from:<URL:en.donga.co.kr/rnd/md02.jsp, 2 pages.
English language abstract of Korean Pat No. KR 10-0440239 (App. No. KR 10-2002-0001172; Pub. No. KR 10-2003-0060458), 1 page.
English language abstract of Korean Pat No. KR 10-0608192 (App. No. KR 10-2003-0023929; Pub. No. KR 10-2004-0090033), 1 page.
English language abstract of Korean Pat No. KR 10-0644369 (App. No. KR 10-2004-0085414; Pub. No. KR 10-2006-0036532), 1 page.
English language abstract of Korean Pat No. KR 10-0979347 (App. No. KR 10-2009-0025399), 1 page.
English language abstract of Korean Pub. No. KR 10-2002-0066024 (App. No. KR 10-2001-0006197), 1 page.
English language abstract of Korean Pub. No. KR 10-2006-0015215 (App. No. KR 10-2004-0064078), 1 page.
English language abstract of Korean Pub. No. KR 10-2011-0027434 (App. No. KR 10-2009-0085522), 1 page.
English language abstract of Korean Pub. No. KR 10-2011-0074116 (App. No. KR 10-2009-0130989), 1 page.
Machine generated English translation of Korean Pat No. KR 10-0440239 (App. No. KR 10-2002-0001172; Pub. No. KR 10-2003-0060458), Korea Intellectual Property Office, 18 pages.
Machine generated English translation of Korean Pat No. KR 10-0608192 (App. No. KR 10-2003-0023929; Pub. No. KR 10-2004-0090033), Korea Intellectual Property Office, 21 pages.
Machine generated English translation of Korean Pat No. KR 10-0644369 (App. No. KR 10-2004-0085414; Pub. No. KR 10-2006-0036532), Korea Intellectual Property Office, 12 pages.
Machine generated English translation of Korean Pat No. KR 10-0979347 (App. No. KR 10-2009-0025399), Korea Intellectual Property Office, 10 pages.
Machine generated English translation of Korean Pub. No. KR 10-2002-0066024 (App. No. KR 10-2001-0006197), Korea Intellectual Property Office, 19 pages.
Machine generated English translation of Korean Pub. No. KR 10-2006-0015215 (App. No. KR 10-2004-0064078), Korea Intellectual Property Office, 14 pages.
Machine generated English translation of Korean Pub. No. KR 10-2011-0027434 (App. No. KR 10-2009-0085522), Korea Intellectual Property Office, 19 pages.
Machine generated English translation of Korean Pub. No. KR 10-2011-0074116 (App. No. KR 10-2009-0130989), Korea Intellectual Property Office, 13 pages.
International Search and Written Opinion, dated Apr. 23, 2014, in connection with International Patent Application No. PCT/KR2014/001103, 10 pages.
International Preliminary Report on Patentability, dated Aug. 18, 2015, in connection with International Patent Application No. PCT/KR2014/001103, 7 pages.
Letter/Written Disclosure of the Supplemental Information Disclosure Statement for the above-referenced application, filed herewith dated Mar. 16, 2017, 2 pages.
Response, submitted Feb. 21, 2017, to the Extended European Search Report and Written Opinion, dated Jul. 25, 2016, in connection with European Patent Application No. 14751188.5, 17 pages.
Letter/Written Disclosure of the Supplemental Information Disclosure Statement for the above-referenced application, filed herewith dated Aug. 10, 2016, 2 pages.
Extended European Search Report, dated Jul. 25, 2016, in connection with European Patent Application No. 14751188.5, 8 pages.

* cited by examiner

[Fig. 1]

N: P<0.05 as T-Test result compared to non-treated group
T: P<0.05 as T-Test result compared to Tyrosur-treated group
F: P<0.05 as T-Test result compared to Fucidin-treated group

[Fig. 2]

N: P<0.05 as T-Test result compared to non-treated group
T: P<0.05 as T-Test result compared to Tyrosur-treated group
F: P<0.05 as T-Test result compared to Fucidin-treated group

FILM-FORMING PHARMACEUTICAL COMPOSITION FOR WOUND HEALING AND METHOD FOR PREPARING THE SAME

RELATED APPLICATIONS

This application is the U.S. National Stage of International Application. No. PCT/KR2014/001103, filed 11 Feb. 2014, which claims benefit of priority to Korean Patent Application KR 10-2013-0015400, filed 13 Feb. 2013, the specification of which is incorporated by reference herein.

TECHNICAL FIELD

The present invention relates to a pharmaceutical composition for forming a film directly on a wound to accelerate wound healing, a use for the same, a treatment method using the same and a method for preparing the same.

BACKGROUND ART

A wound is a type of injury and can be divided into an open wound where skin is torn, punctured or cut and a closed wound such as a bruise, contusion, etc. caused by blunt force. There are various methods for treating wounds. When the wound is slight, it is healed naturally only by cleaning; however, when the wound is a serious open wound, it needs treatment such as cleaning, disinfection, suture and dressing. In the case of most clean open wounds, they do not require antibiotic treatment, but a wound that may be infected with bacteria or an infected wound requires antibiotic treatment.

The wound healing process involves a hemostasis phase including vasoconstriction and hemostatic chain reaction, an inflammatory phase in which immune-related cells are activated, a proliferation phase in which damaged blood vessels are newly formed and fibroblasts are formed, and a maturation and rearrangement phase in which disorganized collagen fibers are rearranged and cross-linked. When a wound occurs, blood comes in contact with collagen to promote platelet aggregation and secretion of inflammatory substances. Fibrin and fibronectin are cross-linked to form a sort of plug, preventing further blood loss. Within an hour after the wound occurs, polymorphonuclear neutrophils arrive at the wound site and become predominant cells in the wound after two days. These neutrophils phagocytize debris and bacteria in the wound. Macrophages are essential for wound healing and replace polymorphonuclear neutrophils the predominant cells in the wound by two days after injury. The main role of these macrophages is to phagocytize bacteria and damaged tissue and they also debride damaged tissue by releasing proteases. These macrophages also secrete growth factors involved in the proliferation phase after post-wounding, contributing to pushing the wound healing process into the next phase. About two or three days after the wound occurs, fibroblasts begin to enter the wound site, marking the onset of the proliferative phase. Angiogenesis, which is important for this period, occurs concurrently with fibroblast proliferation when endothelial cells migrate to the wound site. Simultaneously with angiogenesis, fibroblasts begin accumulating in the wound site. Fibroblasts begin to increasing as the inflammatory phase is ending between two and five days after the wound. Their numbers peak between one and two weeks after wound. While one of the most important functions of such fibroblasts is the production of collagen, the production of collagenase and other factors degrading collagen is also one of their functions, and the production occurs more rapidly than the degradation in the wound. Granulation tissue consists of fibroblasts, inflammatory cells, endothelial cells, new blood vessels, etc. The formation of granulation tissue in an open wound allows the reepithelialization phase to take place, as epithelial cells migrate and form a barrier between the wound and the environment. Contraction is a key phase of wound healing and begins as fibroblasts differentiate into myofibroblasts. When the levels of collagen production and degradation equalize, the maturation and rearrangement phase of wound repair is started. During maturation, type III collagen is gradually replaced with type I collagen, and fibroblasts are rearranged and cross-linked, resulting in increased tissue tension. This phase can last for a year or longer as the wound type.

Wound treatment methods have been studied for a long time and a variety of products have been sold in the market. Disinfecting products containing oxygenated water, povidone-iodine, ethyl alcohol, isopropyl alcohol, etc. used to disinfect the wound surface and dressing products such as gauze, bandage, etc. which facilitate hemostasis and protect the wound surface to prevent secondary infections, etc. have been sold. Moreover, products containing antibiotics, such as mupirocin, fusidic acid and salts thereof, tyrothricin, etc., used for a wound that may concern infection or be infected from such wound, or products containing a titrated extract of Centella asiatica alone or in combination with steroid or antibiotics have been sold usually in the form of a gel or ointment. Representative products include Fucidin® ointment, Tyrosur® gel, Madecassol®, etc.

The use of these gel or ointment formulations has the following several problems. Upon application to the wound, the formulation on the wound surface is not present for a long time due to external contact with gauze, clothing, etc. Therefore, the drug is not in constant contact with the wound surface and thus is not continuously delivered to the wound. Moreover, when the wound is exposed to the outside through the area from which the drug is removed, the probability of re-infection will increase. Further, the exposed wound causes the patient to feel pain by other external physical stimuli. Therefore, many patients use disposable bandage, gauze or bandage in combination with the use of these formulations to cope with these drawbacks, but it is very inconvenient to replace these dressings for each application. In addition, typical products containing antibiotics alone exhibit antibiotic activity in infected wound sites and thus they only prevent infection in infected wound sites. However, the effect of promoting wound healing that make a swift recovery is not yet known.

Therefore, the present inventors have conducted continuous research to overcome the drawbacks of the above-described preparations. As a result, they invented a wound healing gel, which is usually in the form of a gel during storage and usage, converted into the form of a film upon application to a wound site to protect the wound site, continuously deliver drugs to the wound site, and is not removed from the wound site by clothing, gauze, etc.

Several formulations containing pharmaceutical ingredients as active ingredients and forming films upon application to the skin have been known in the art. Korean Patent No. 0551930, Korean Patent Publication No. 2008-0049797 and Korean Patent No. 1996-0009415 disclose compositions comprising active substances as well as hydrophilic thickeners, hydrophobic polymers such as octylacrylamide acrylate copolymer, aminoalkyl methacrylate copolymer, ammonio methacrylate copolymer, ethyl acrylate methyl methacrylate, and volatile solvents such as ethanol. However, these compositions are separated with exudates after the formation of films on the wounds due to the high content of hydrophobic polymers and stimulate the wound surfaces due to the high content of organic solvents and thus these compositions are not suitable for wound healing. Moreover, Korean Patent No. 0979347 discloses an antifungal composition comprising terbinafine or a salt thereof and trimethyloxysilicate for forming a film after application to the skin. However, this composition is not also suitable for wound healing due to the above-described problems such as the high content of hydrophobic substance and organic solvent.

Korean Patent No. 0748390 discloses a sustained release film formulation for wound healing comprising epidermal growth factor as well as chitosan, glycerin, etc. However, this technology reduces the adhesion between the wound and the formulation, because it does not form a film directly on the wound surface. Therefore, the drug delivery and the protection of the wound surface are not complete. In particular, in the case of an irregular wound which a portion of the skin is taken away, the adhesion is further reduced.

Korean Patent Publication No. 2011-0027434 discloses a composition for forming a water-repellent film with sustained drug delivery ability, comprising sodium fusidate, ethyl cellulose, soybean oil and ethanol. As mentioned above, the preparation having a high content of organic solvent causes pain upon application to the skin and reduces the rate of wound healing.

Korean Patent Publication No. 2002-0066024 discloses an ointment composition and film comprising water-soluble chitosan, chemically modified with water, and heparin as active substances.

Korean Patent No. 0440239 discloses a method for the preparation of hydrogels comprising polyvinyl alcohol, polyvinylpyrrolidone and chitosan. The composition has a high content of polymer and thus the water in the gel is not evaporated. Therefore, it cannot form a film.

Korean Patent Nos. 0608192 and 0644369 disclose technologies for producing sponges by freeze-drying dissolved chitosan. These technologies also do not form a film directly on the wound surface and thus the adhesion to the wound is reduced. Therefore, these technologies have the same problems as described above.

Korean Patent Publication Nos. 2012-0023653 and 2012-0022930 disclose medicinal creams comprising fusidic acid, sulphadiazine and chitosan as active substances as well as at least one of primary and secondary emulsifiers, wax, acid and water. These compositions contain a large amount of non-volatile, lipophilic and semi-solid materials such as paraffin, cetostearyl alcohol, etc. to give appropriate viscosity. However, the compositions disclosed in the above inventions have poor film formation properties, and even if the film is formed, it is easily destroyed by external mechanical stimuli.

The present inventors have intensively studied to overcome the drawbacks associated with the conventional preparations containing the above-described antibiotics. As a result, the present inventors invented a formulation which comprises an active substance, maintains the form of a gel during storage period, and forms a film upon application to a wound. We found that the composition of the present invention has a simpler configuration than the prior art, has excellent film-forming effect and high mechanical strength, and has excellent properties that form a film directly on a wound surface upon application to a wound site to provide high adhesion to the wound and to be easily removed from normal tissue of healed wound, thus completing the present invention.

DISCLOSURE OF INVENTION

Technical Problem

An object of the present invention is to provide a pharmaceutical composition, a use for the same, a treatment method using the same, and a method for preparing the same, which comprises an active substance, maintains the form of a gel before application to a wound, forms a film directly after application to protect the wound, continuously delivers drugs, prevents the formulation from being lost by physical contact with gauze, bandage, etc., and prevents re-infection by bacteria. Therefore, it overcomes the drawbacks of conventional preparations (such as gels, ointments, etc) for wound healing and improves the wound healing effect.

Solution to Problem

To achieve the above objects, the present invention provides a composition which forms a film on a wound after application thereto and maximizes the wound healing effect.

The present invention provides a pharmaceutical composition for wound healing, which forms a film upon application to the skin, the pharmaceutical composition for wound healing comprising: (a) a pharmaceutically active substance; (b) a chitosan or a salt thereof as a film-forming substance; and (c) a solvent for dissolving the chitosan, wherein the film-forming substance is contained in an amount of 0.3 wt % or higher, preferably 0.4 to 20 wt % and more preferably 0.5 to 15 wt % with respect to the total weight of the composition, and wherein the composition further comprises a cream base component and the weight ratio of the film-forming substance to the cream base component is 1:70, 1:60, 1:50, 1:40, 1:30, 1:25 or more.

In one embodiment, the wound is an incised wound, a lacerated wound, a penetrating wound, a perforated wound, a puncture wound, an open wound, a subcutaneous wound, a closed wound and a combination thereof. In another embodiment the wound is a consequence of a disease or disorder, surgery, accident and a combination thereof. In yet another embodiment, the wound is external wound, internal wound and a combination thereof.

Conventional chitosan-containing formulations contain a small amount of chitosan, contain chitosan at levels that do not form a film upon application to the skin, or contain a large amount of cream base component, etc., which makes it impossible to form a film upon application to the skin. However, in the present invention, the composition contains chitosan in an amount suitable to form a film, i.e., in an amount of 0.3 wt % or higher, preferably 0.4 to 20 wt % and more preferably 0.5 to 15 wt % with respect to the total weight of the composition, so as to form and maintain a film having a suitable strength, preferably a strength of 10 N or higher upon application to the skin.

In particular, the composition of the present invention does not contain a cream base component that interferes with the film formation. Preferably, the composition of the present invention contains a small amount of the cream base component, and the weight ratio of the film-forming substance to the cream base component is 1:70, 1:60, 1:50, 1:40, 1:30, 1:25 or more. If the weight ratio of the film-forming substance to the cream base component is lower than 1:70, it is impossible to form a film having a sufficient strength upon application of the composition to the skin. Therefore, the composition of the present invention, which contains the cream base component in a predetermined ratio with respect to the chitosan, can form a film useful for wound healing on a wound surface as the solvent is evaporated or volatilized upon application to the skin.

These cream base components are fully described in "Handbook of Pharmaceutical Excipients, 6th edition, Pharmaceutical Press". The cream base components that interfere with the film formation by the film-forming substances in the composition of the present invention are well known in the art. In general, the cream formulations are in the form of an emulsion, in which an oil phase is dispersed in water, the emulsion comprising an oil phase, an emulsifier and a water phase. The cream base components mentioned in the specification refer to the oil phase and the emulsifier, and those skilled in the art can easily understand the meaning and examples of the cream base components. These cream base components include any materials, which interfere with the film formation by chitosan upon application of the composition of the present invention to the skin and form a formulation in the form of a cream when it is present in a predetermined amount, and are not limited to those described in this specification. Examples of the cream base component may include isopropyl palmitate, cetyl palmitate, paraffin, trioctanoin, soybean oil, sesame oil, olive oil, liver oil, oleic acid, stearic acid octyldodecanol, octyldodecyl myristate, Silicone compound as dimethicone or Simethicone, stearyl alcohol, stearyl glycyrrhetinate, polyoxyl stearate, squalane, cetostearyl alcohol, cetomacrogol, cetanol, sorbitan sesquioleate, Vaseline, white beeswax, yellow beeswax, myristyl alcohol, isopropyl myristate, sorbitan monooleate, sorbitan monostearate, glycerin monostearate, lecithin, hydrogenated castor oil, caprylic-capric triglyceride, lanolin, oleoyl macrogolglycerides, etc., but not limited thereto. The film-forming composition of the present invention is different from the conventional chitosan-containing formulations in that it contains the cream base component in a ratio that does not interfere with the film formation by chitosan.

The film-forming composition of the present invention may further comprise at least one additive selected from the group consisting of an acid, a plasticizer, a thickener, a surfactant, a preservative, a flavoring agent and a humectant. Here, the amount of each additive used in the present invention is 30 wt % or less, preferably 0.1 to 20 wt %, more preferably 0.1 to 16 wt % and still more preferably 0.25 to 10 wt % with respect to the total weight of the composition.

According to an embodiment of the present invention, the present invention provides a pharmaceutical composition for wound healing, comprising: (a) a pharmaceutically active substance; (b) a chitosan or a salt thereof as a film-forming substance; (c) a solvent for dissolving the chitosan, and (d) an additive selected from the group consisting of an acid, a plasticizer, a thickener, a surfactant, a preservative, a flavoring agent, a stabilizer, a defoamer, an analgesic agent, an antioxidant, an adhesive, a gellant, an emulsifier, an astringent, an opacifier, a humectant and mixtures thereof.

According to another embodiment of the present invention, the present invention provides a pharmaceutical composition for wound healing, comprising: (a) at least one pharmaceutically active substance selected from the group consisting of tyrothricin, fusidic acid or a salt thereof, neomycin sulfate or a salt thereof, hydrocortisone, titrated extract of Centella asiatica and combinations thereof; (b) a chitosan or a salt thereof as a film-forming substance in an amount of 0.4 to 20 wt % and preferably 0.5 to 15 wt % with respect to the total weight of the composition; and (c) at least one solvent selected from the group consisting of water, ethanol, isopropyl alcohol and mixtures thereof, wherein the composition further comprises a cream base component and the weight ratio of the film-forming substance to the cream base component is 1:70, 1:60, 1:50, 1:40, 1:30, 1:25 or more.

According to still another embodiment of the present invention, the present invention provides a pharmaceutical composition for wound healing, comprising: (a) at least one pharmaceutically active substance selected from the group consisting of tyrothricin, fusidic acid or a salt thereof, neomycin sulfate or a salt thereof, hydrocortisone, titrated extract of Centella asiatica and combinations thereof in an amount of 0.1 to 10 wt %, with respect to the total weight of the composition; (b) a chitosan or a salt thereof as a film-forming substance in an amount of 0.4 to 20 wt % and preferably 0.5 to 15 wt % with respect to the total weight of the composition; and (c) at least one solvent selected from the group consisting of water, ethanol, isopropyl alcohol and mixtures thereof in an appropriate amount, preferably in the residual amount other than the main component and other components, wherein the composition further comprises a cream base component and the weight ratio of the film-forming substance to the cream base component is 1:70, 1:60, 1:50, 1:40, 1:30, 1:25 or more.

According to yet another embodiment of the present invention, the present invention provides a pharmaceutical composition for wound healing, comprising: (a) a pharmaceutically active substance such as tyrothricin in an amount of 0.1 to 10 wt % with respect to the total weight of the composition; (b) a chitosan or a salt thereof as a film-forming substance in an amount of 0.4 to 20 wt %, preferably 0.5 to 15 wt % and more preferably 1 to 10 wt % with respect to the total weight of the composition; (c) at least one solvent selected from the group consisting of water, ethanol, isopropyl alcohol and mixtures thereof in an appropriate amount, preferably in the residual amount other than the main component and other components; (d) an acid, preferably lactic acid, in an amount of 0.20 to 20 wt %, preferably 0.25 to 10 wt % and more preferably 0.5 to 7.5 wt % with respect to the total weight of the composition; and (e) a thickener, preferably poloxamer, in an amount of 0.2 to 10 wt % with respect to the total weight of the composition, wherein the composition further comprises a cream base component and the weight ratio of the film-forming substance to the cream base component is 1:70, 1:60, 1:50, 1:40, 1:30, 1:25 or more.

The composition of the present invention can be effectively used for wound healing to treat a wound or infectious disease.

Hereinafter, the present invention will be described in more detail.

The composition of the present invention comprises at least one physiologically or pharmaceutically active substance. The physiologically or pharmaceutically active substance is a drug useful for wound healing and includes those commonly used in the art. Examples of the physiologically or pharmaceutically active substance may include antibiotics, wound healing accelerants, disinfectants, local anesthetics or anti-inflammatory agents.

For example, the active substance used in the composition of the present invention may include: penicillin antibiotics such as amoxicillin, ampicillin, moxalactam, piperacillin, sulbenicillin, talampicillin, or salts thereof; cephalosporin antibiotics such as cefadroxil, cefatrizine, cefradine, cefaclor, cefotiam, cefuroxime, cefixime, ceftriaxone, cefepime, cefpirome, or salts thereof; betalactam antibiotics such as aztreonam, meropenem, or salts thereof; aminoglycoside antibiotics such as amikacin, arbekacin, isepamicin, sisomycin, tobramycin, vancomycin, or salts thereof; macrolide antibiotics such as azithromycin, clarithromycin, erythromycin, midecamycin, roxithromycin, spiramycin, or salts thereof; quinolone antibiotics such as ciprofloxacin, enoxacin, gatifloxacin, levofloxacin, lomefloxacin, tosufloxacin, or salts thereof; tetracycline antibiotics such as doxycycline, methacycline, minocycline, tetracycline, or salts thereof; or any other antibacterial substances having different mechanisms. Preferably, the active substance may be bacitracin, chloroxylenol, clindamycin, fusafungine, gentamicin, mafenide, mupirocin, neomycin, nitrofurazone, oxytetracycline, retapamulin, silver sulfadiazine, tyrothricin, fusidic acid, polymyxin, nystatin, mupirocin, or salts thereof.

Moreover, the composition of the present invention may contain a disinfectant or sanitizer for disinfection in the early stage of the wound healing as an active substance. Examples of the disinfectant or sanitizer may include any main components, which are known for their wound disinfection, such as Glutaral Concentrate, benzalkonium, benzethonium, chlorohexidine, cresol, ethanol, isopropyl ethanol, povidone-iodine, silver nitrate, or salts thereof.

Furthermore, the composition of the present invention may contain a wound healing accelerant as an active substance for accelerating the wound healing. Examples of the wound healing accelerant may include water-soluble azulene, policresulen, becaplermin, Centella asiatica extract, dexpanthenol, keratinocytes, lysozyme, polydeoxyribonucleotide, solcoseryl 120 concentrate, trafermin, or salts thereof.

In addition, the composition of the present invention may contain a local anesthetic as an active substance for eliminating pain of the initial wound. Examples of the local anesthetic may include benzocaine, bupivacaine, levobupivacaine, lidocaine, mepivacaine, procaine, ropivacaine, tetracaine, prilocaine, or salts thereof.

Additionally, the composition of the present invention may contain an anti-inflammatory agent as an active substance for eliminating inflammation at the wound site. Examples of the anti-inflammatory agent may include alclometasone, amcinonide, beclomethasone, budesonide, clobetasol, desonide, desoxymethasone, dexaltin NK, dexamethasone, diflucortolone, fluocinolone, fluocinonide, fluticasone, halcinonide, hydrocortisone, methylprednisolone, prednicarbate, prednisolon, triamcinolone, or salts thereof.

The composition of the present invention may contain at least one of the above-listed substances that can be used for wound healing, but not limited thereto. Preferably, the pharmaceutically active substance may comprise at least one selected from the group consisting of tyrothricin, fusidic acid or a salt thereof, neomycin sulfate or a salt thereof, hydrocortisone, titrated extract of Centella asiatica and combinations thereof. The amount of the active substance contained in the composition of the present invention is in a concentration range with the suggestion that their safety and effectiveness have been proven, preferably in a range of 0.3 to 2 times the commercially available concentration of each component.

The composition of the present invention comprise chitosan as a film-forming substance, which is usually present in the form of a gel, sol, etc. during storage and forms a film on a wound site upon application to the human body.

Chitosan can be obtained by deacetylation of chitin from crustaceans and is a linear polysaccharide composed of randomly distributed β-(1-4)-linked D-glucosamine and N-acetyl-D-glucosamine. The properties of polysaccharide vary depending on the degree of deacetylation, and the desired degree of deacetylation is 80%, 82%, 84%, 86%, 88%, 90% or higher. In the present invention, the chitosan serves as a thickener that maintains the form of a gel formulation and does not flow during use to conveniently apply to the skin as well as the role of the film-forming substance. The molecular weight of the chitosan used in the present invention is not limited to any particular molecular weight, and in the case of a low molecular weight, the chitosan may contain a thickener to maintain the gel formulation or can be administered in the form of a thin gel without containing an additional thickener. Moreover, the chitosan of the present invention is in the form of a free base or salt or derivatives and if the chitosan is in the form of a salt, an acid may not be required. In the present invention, the chitosan may be prepared by a method known in the art or may be commercially available. The content of chitosan in the composition of the present invention shall be an amount sufficient to maintain a proper viscosity and to form a film having a sufficient strength upon application to the skin. The amount of chitosan may preferably be 0.3 wt % or higher with respect to the total weight of the composition, more preferably 0.4 wt % or higher and does not exceed 20 wt % and still more preferably 0.5 wt % or higher and does not exceed 15 wt %.

The composition of the present invention may contain an acid for dissolving chitosan. Examples of the acid for dissolving the chitosan may include sulfuric acid, fluorosulfuric acid, nitric acid, phosphoric acid, hydroboric acid, boric acid, ascorbic acid, acetic acid, citric acid, propionic acid, formic acid, gluconic acid, lactic acid, oxalic acid, tartaric acid, malic acid, adipic acid, maleic acid, succinic acid, etc., and these acids may be used alone or in combinations. The amount of the acids may preferably be 0.2 to 20 wt % with respect to the total weight of the composition. Preferably, lactic acid is used.

The composition of the present invention may also contain a solvent for dissolving chitosan. The solvent serves to maintain the preparation in the form of a fluid before application to the skin and to volatilize after application to the wound, thus forming a film on the wound surface.

In the composition of the present invention, the solvent for dissolving the chitosan may preferably be selected from the group consisting of water, lower alcohol having 1 to 4 carbon atoms and mixtures thereof, more preferably be selected from the group consisting of ethanol, isopropyl alcohol and mixtures thereof. These solvents are used in an amount suitable to control the active substance. Moreover, these solvents are evaporated or volatilized upon application of the composition to the skin such that a film can be formed on the skin surface to which the composition of the present invention is applied.

The composition of the present invention may contain a solvent for dissolving an active substance as well as the chitosan. The solvent serves to maintain the preparation in the form of a fluid before application to the skin and to volatilize after application to the wound, thus forming a film on the wound surface. The solvent of the present invention may preferably be isopropyl alcohol, ethyl alcohol, ethyl acetate, acetone, water or mixtures thereof, more preferably isopropyl alcohol, ethyl alcohol, water or mixtures thereof, which are less irritating to the wound surface. An appropriate amount of the solvent may be one that can maintain the active substance at a constant concentration.

The composition of the present invention may also comprise a plasticizer. The plasticizer serves to facilitate the production of preparations and prevent precipitation of the active substances from the preparations by assisting the dissolution of the active substances in the composition of the present invention. Moreover, after the formation of the film on the wound surface, the plasticizer serves to soften the strength of the film formed so as to prevent destruction of the film due to contraction of the skin and maintain the film. Therefore, it provides functional and aesthetic excellence. Examples of the plasticizer that can be used in the present invention may be selected from the group consisting of propylene glycol, polyethylene glycol, propylene carbonate, Labrasol® PEG-8 caprylic/capric glycerides, Transcutol® 2-(2-ethoxyethoxy)ethanol, Labrafac™ propylene glycol dicaprylate dicaprate, Plurol Oleique® polyglyceryl-6 dioleate, Lauroglycol™ propylene glycol laurate, Capryol™ propylene glycol caprylate, Labrafil® lauroyl, linoleoyl and oleoyl polyoxylglycerides, Miglyol® fractionated coconut oil or caprylic/capric triglycerides, glycerin and mixtures thereof and may preferably be contained in an amount of 0.2 to 10 wt % with respect to the total weight of the composition.

The composition of the present invention may further comprise a thickener. The thickener may be selected from the group consisting of hydroxypropyl cellulose, hydroxypropylmethyl cellulose, hydroxyethyl cellulose, xanthan gum, locust bean gum, arabic gum, guar gum, carbomer, polyethylene oxide, poloxamer and mixtures thereof, and the thickener may preferably be contained in an amount of 0.2 to 10 wt % with respect to the total weight of the composition, which can maintain the viscosity to a degree that can supply the insufficient thickening ability of the chitosan.

The composition of the present invention may further comprise a surfactant. When the active substance is poorly water soluble, the surfactant improves the solubility of the active substance in the preparation to prevent precipitation. Moreover, the surfactant increases the miscibility of other hydrophobic materials in the preparation to maintain the formulation stable. Furthermore, in the case of a poor water-soluble active substance, the surfactant increases the penetration of drugs into the wound. For example, in the case of tyrothricin used as an antibiotic, its solubility in water is significantly reduced and thus precipitates are formed in a preparation containing excess water phases. However, in the case of an ethylene oxide/propylene oxide copolymer (poloxamer) used as a surfactant, it maintains the dissolved state. Examples of the surfactant that can be added to the composition of the present invention may include nonionic surfactants such as polysorbate 20, polysorbate 40, polysorbate 60, polysorbate 80, polyethylene hydroxystearate (e.g., Solutol HS15), polyethoxylated castor oil (e.g., Cremophor EL, Cremophor RH40, Cremophor RH60), ethylene oxide/propylene oxide copolymer (e.g., poloxamer 124, poloxamer 188, poloxamer 407), stearoyl macrogol-32 glycerides, lauroyl macrogol-32 glycerides, propylene glycol monocaprylate, caprylocaproyl macrogol-8 glycerides, etc. or ionic surfactants such as sodium lauryl sulfate, sodium docusate, benzalkonium chloride, benzethonium chloride, etc. The amount of the surfactant used in the present invention may be an amount that is sufficient for the above objectives and may preferably be 0.1 to 10 wt % with respect to the total weight of the composition.

The composition of the present invention may further comprise a preservative. Examples of appropriate preservatives may include, but not limited to, quaternary ammonium compounds such as benzalkonium chloride, benzethonium chloride, cetrimide, dequalinium chloride and cetylpyridinium chloride; alcohol compounds such as chlorobutanol, phenylethyl alcohol and benzyl alcohol; parabens such as methylparaben, ethylparaben, propylparaben and butylparaben; antibacterial esters such as ester of parahydroxybenzoic acid; and other antibacterial agents such as chlorohexidine, chlorocrosol, benzoic acid, polymixine and phenoxyethanol. Preferably, the preservative may comprise at least one selected from the group consisting of sodium benzoate, phenoxyethanol, benzyl alcohol, methylparaben, imidazolidinyl urea and diazolidinyl urea. The preservatives may preferably be contained in an amount of 0.1 to 10 with respect to the total weight of the composition.

The composition of the present invention may further comprise other additives typically added to usual pharmaceutical preparations for external application. For example, the additives may include preservatives, flavoring agents, bases, humectants, stabilizers, defoamers, analgesic agents, antioxidants, thickeners, gallants, emulsifiers, astringents, opacifiers, etc., and their examples are fully described in "Handbook of Pharmaceutical Excipients, 6th edition, Pharmaceutical Press". Those skilled in the art can select these additives and use them in the formulation of the present invention without any technical difficulties. Moreover, these additives are typically added to pharmaceutical preparations for external application, and those that do not interfere with the film formation upon application of the composition of the present invention can be appropriately used. Even when these additives correspond to the cream base components described in this specification, these additives can be used in an amount that is preferably adjusted within the range described in this specification.

The composition of the present invention is in the form of a semi-solid such as a liquid, gel, or ointment before use, but forms a film after application to the skin. The form of the active substance present in the formulation may be a suspension in which fine particles are suspended in a solid state or an emulsion in which fine particles are dissolved in an oil phase. Moreover, when the active substance itself is well dissolved or solubilized, it may be present in the form of a liquid. The formulations for the composition of the present invention may be prepared by a typical pharmaceutical production method such as a method described in "Remington's Pharmaceutical Science, Mack Publishing Co.".

Moreover, the present invention provides a method of wound healing, comprising treating to a subject a therapeutically effective amount of a pharmaceutical composition. The wound healing method of the present invention comprises alleviative and curative treatment. Preferably, the method is used for treatment of humans.

The term "pharmaceutically effective" means approved by a regulatory agency of the government or listed in Pharmacopeia or other generally recognized pharmacopeia for use in animals, and more particularly in humans.

The composition of the present invention is intended to be applied topically and directly to the wound. In one embodiment, the composition is in the form of an ointment, a liquid or a gel which is spread directly onto the wound (e.g. skin, etc) and forms a film upon application to the wound.

Furthermore, the present invention relates to a use of the pharmaceutical composition of the present invention for wound healing.

Moreover, the present invention relates to a use of composition for manufacturing a pharmaceutical composition for wound healing.

The details mentioned in the use, composition and method of the present invention are equally applied unless they are contradictory.

Advantageous Effects of Invention

The present invention provides the following effects:

First, upon application of the composition in a typical form to the skin, it forms a film to prevent the formulation being separated from the wound surface by physical contact, thus reducing the use of bandage or gauze and the number of uses.

Second, the film directly forms on the wound surface and increases the adhesion to the wound. In particular, in the case of an irregular wound, the adhesion is further increased.

Third, the formed film allows drugs to be continuously delivered to the wound surface, thus increasing the wound healing effect.

Fourth, the film formed on the wound surface can protect the wound from being infected by external bacteria, etc.

Fifth, it prevents both edges of an incised wound, such as a wound cut by a knife, from being opened, thus improving the treatment of the incised wound.

Lastly, the composition of the present invention tends to adhere to the wound surface only in a humid environment and thus it is selectively separated from the healing site as the wound healing process continues.

MODE FOR THE INVENTION

The present invention will be described in more detail with reference to the following Examples. However, the following Examples are intended to illustrate the present invention, and the present invention is not limited by the following Examples.

EXAMPLES 1 TO 6

Preparation of Film-Forming Gels Containing Tyrothricin and Water

Tyrothricin, ethanol, propylene glycol, cetylpyridinium chloride and a flavoring agent were mixed in amounts described in the following Table 1 and completely dissolved using an overhead mixer, thus preparing liquid 1. Apart from above liquid 1, water was placed in a Homo-Agi Mixer, chitosan was added and dispersed, and lactic acid was further added and dissolved. To the dissolved liquid, poloxamer 407 (and polysorbate 80) was further added and dissolved. Liquid 1 containing tyrothricin was added to the resulting solution and completely dissolved, thus preparing film-forming gels containing tyrothricin.

When the preparations of the following Examples were applied to the skin, transparent films were formed in all cases after 10 to 20 minutes.

TABLE 1

| Ingredients | Example 1 | Example 2 | Example 3 | Example 4 | Example 5 | Example 6 |
|---|---|---|---|---|---|---|
| Tyrothricin | 0.1 | 0.1 | 0.1 | 0.1 | 0.1 | 0.1 |
| Chitosan, low molecular weight* | — | 4 | — | 10 | — | — |
| Chitosan, high molecular weight** | 4 | — | — | — | 0.5 | 4 |
| Chitosan chloride*** | — | — | 4 | — | — | — |
| Poloxamer 407 | 2.5 | 5 | 2.5 | — | 8 | 0.1 |
| Polysorbate 80 | — | — | — | — | — | 1 |
| Lactic acid | 2 | 2 | 2 | 6 | — | 2 |
| Propylene glycol | 1 | 1 | 1 | 1 | — | 1 |
| Cetylpyridinium chloride | 0.05 | 0.05 | 0.05 | 0.05 | 0.05 | 0.05 |
| Flavoring agent | Quantum satis | Quantum satis | Quantum satis | Quantum satis | Quantum satis | Quantum satis |
| Ethanol | 1 | 1 | 1 | 1 | 1 | 1 |
| Purified water | Balance up to 100 g | Balance up to 100 g | Balance up to 100 g | Balance up to 100 g | Balance up to 100 g | Balance up to 100 g |

*Molecular weight of 100,000 or less
**Molecular weight of 100,000~2,000,000 or less
***Prepared by treating chitosan with hydrochloric acid and solubilizing in the water

EXAMPLES 7 TO 9

Preparation of Film-Forming Gels Containing Tyrothricin in Different Concentrations and Water Film-forming gels having different chitosan concentrations as described in the following Table 2 were prepared by the same method as Example 1. When the preparations of the following Examples were applied to the skin, transparent films were formed in all cases after 10 to 20 minutes.

TABLE 2

| Ingredients | Example 7 | Example 8 | Example 9 |
|---|---|---|---|
| Tyrothricin | 0.1 | 0.1 | 0.1 |
| Chitosan, high molecular weight | 0.5 | 1 | 2 |
| Poloxamer 407 | 2.5 | 2.5 | 2.5 |
| Lactic acid | 0.25 | 0.5 | 1 |

TABLE 2-continued

| Ingredients | Example 7 | Example 8 | Example 9 |
|---|---|---|---|
| Propylene glycol | 1 | 1 | 1 |
| Cetylpyridinium chloride | 0.05 | 0.05 | 0.05 |
| Flavoring agent | Quantum satis | Quantum satis | Quantum satis |
| Ethanol | 1 | 1 | 1 |
| Purified water | Balance up to 100 g | Balance up to 100 g | Balance up to 100 g |

EXAMPLE 10

Preparation of Film-Forming Liquid Containing Tyrothricin and Water

Tyrothricin, ethanol, propylene glycol, cetylpyridinium chloride and a flavoring agent were mixed in amounts described in the following Table 3 and completely dissolved using an overhead mixer, thus preparing liquid 1. Separately, water and chitosan were placed and dispersed in another overhead mixer, and lactic acid was further added to dissolve the chitosan. Liquid 1 containing tyrothricin was added to the chitosan solution and completely dissolved, thus preparing a film-forming liquid containing tyrothricin. When the preparation of the following Example 10 was applied to the skin, a transparent film was formed after 10 to 20 minutes.

TABLE 3

| Ingredients | Example 10 |
|---|---|
| Tyrothricin | 0.1 |
| Chitosan, low molecular weight | 4 |
| Lactic acid | 2.5 |
| Propylene glycol | 1 |
| Cetylpyridinium chloride | 0.05 |
| Flavoring agent | Quantum satis |
| Ethanol | 1 |
| Purified water | Balance up to 100 g |

EXAMPLES 11 TO 14

Preparation of Film-Forming Gels Containing Tyrothricin, Water and Ethanol

Tyrothricin, ethanol (1 g), propylene glycol, cetylpyridinium chloride, benzyl alcohol and a flavoring agent were mixed in amounts described in the following Table 4 and completely dissolved using an overhead mixer, thus preparing liquid 1. Separately, chitosan was dispersed in water (40 g) using an overhead mixer and then lactic acid was added to dissolve the chitosan, thus preparing liquid 2. Ethanol (45 g) was placed in a Homo-Agi Mixer, and hydroxypropyl cellulose was added and dissolved. Liquid 1 was placed in the Homo-Agi Mixer and stirred, and then liquid 2 was added and completely dissolved, thus forming film-forming gels containing tyrothricin. When the preparations of the following Examples were applied to the skin, transparent films were formed in all cases after 8 to 15 minutes.

TABLE 4

| Ingredients | Example 11 | Example 12 | Example 13 | Example 14 |
|---|---|---|---|---|
| Tyrothricin | 0.1 | 0.1 | 0.1 | 0.1 |
| Chitosan, low molecular weight | 2 | 2 | 3 | 2 |
| Hydroxypropyl cellulose HF | 1.5 | 2 | — | — |
| Hydroxypropyl cellulose MF | — | — | 2 | 2.5 |
| Lactic acid | 1.33 | 1.33 | 1.33 | 1.33 |
| Propylene glycol | 1 | 1 | 1 | 1 |
| Benzyl alcohol | 0.1 | — | — | 0.1 |
| Cetylpyridinium chloride | 0.05 | — | — | 0.05 |
| Flavoring agent | Quantum satis | Quantum satis | Quantum satis | Quantum satis |
| Ethanol | 46 | 46 | 46 | 46 |
| Purified water | Balance up to 100 g | Balance up to 100 g | Balance up to 100 g | Balance up to 100 g |

EXAMPLES 15 AND 16

Preparation of Film-Forming Gels Containing Sodium Fusidate

Sodium fusidate or sodium fusidate and hydrocortisone, water (20 g), polysorbate 80, propylene glycol, ethanol and a flavoring agent were mixed in amounts described in the following Table 5 and completely dissolved or dispersed using an overhead mixer, thus preparing liquid 1. Separately, the rest of water was added to a Homo-Agi mixer, chitosan was added and dispersed, and then lactic acid was added to dissolve the chitosan. To the resulting solution, poloxamer 407 was further added and dissolved by stirring. Liquid 1 was placed in the Homo-Agi Mixer and stirred, and then liquid 2 was added and completely dissolved, thus forming film-forming gels containing sodium fusidate, etc. When the preparations of the following Examples were applied to the skin, transparent films were formed in all cases after 10 to 20 minutes.

TABLE 5

| Ingredients | Example 15 | Example 16 |
|---|---|---|
| sodium fusidate | 2 | 2 |
| Hydrocortisone | — | 1 |
| Chitosan, high molecular weight | 4 | 4 |
| Poloxamer 407 | 2 | 2 |
| Polysorbate 80 | 1 | 2 |
| Lactic acid | 2 | 2 |
| Propylene glycol | 1 | 1 |
| Cetylpyridinium chloride | 0.05 | 0.05 |
| Flavoring agent | Quantum satis | Quantum satis |
| Ethanol | 1 | 1 |
| Purified water | Balance up to 100 g | Balance up to 100 g |

EXAMPLES 17 TO 20

Preparation of Film-Forming Gels Containing Titrated Extract of Centella asiatica A titrated extract of Centella asiatica (Example 17), the titrated extract of Centella asiatica and neomycin sulfate (Example 18), or the titrated extract of Centella asiatica, neomycin sulfate and hydrocortisone (Example 19) were mixed with propylene glycol, ethanol, ethylene glycol stearate, a flavoring agent and polysorbate 80 in amounts described in the following Table 6 and dissolved or dispersed. Cetylpyridinium chloride was added thereto and homogeneously mixed by heating, thus preparing liquid 1. Separately, water was placed in a Homo-Agi mixer, and then chitosan was added and dispersed. Lactic acid was added thereto and dissolved, and then liquid 1 was added and stirred, thus preparing film-forming gels containing the respective active ingredients. When the preparations of the following Examples were applied to the skin, transparent films were formed in all cases after 10 to 20 minutes.

TABLE 6

| Ingredients | Example 17 | Example 18 | Example 19 | Example 20 |
|---|---|---|---|---|
| Titrated extract of Centella asiatica | 1 | 1 | 1 | 1 |
| Neomycin sulfate | — | 1 | 1 | — |
| Hydrocortisone | — | — | 1 | — |
| Chitosan, high molecular weight | 4 | 4 | 4 | 1 |
| Cetostearyl alcohol | — | — | — | 8.5 |
| Ethylene glycol stearate | 5 | 5 | 5 | 8.5 |
| Polysorbate 80 | 5 | 5 | 5 | 7 |
| Lactic acid | 2 | 2 | 2 | 2 |
| Propylene glycol | 5 | 5 | 5 | 5 |
| Cetylpyridinium chloride | 0.05 | 0.05 | 0.05 | 0.05 |
| Flavoring agent | Quantum satis | Quantum satis | Quantum satis | Quantum satis |
| Ethanol | 1 | 1 | 1 | 1 |
| Purified water | Balance up to 100 g | Balance up to 100 g | Balance up to 100 g | Balance up to 100 g |

COMPARATIVE EXAMPLE 1

Preparation of Cream Formulation Containing Chitosan

A cream formulation containing 0.25% (w/w) chitosan and silver sulfadiazine was prepared from the ingredients of Example 1 disclosed in Korean Patent Publication No. 2012-0022930.

| Sulfadiazine silver 1% + Chitosan cream | | |
|---|---|---|
| Sample No. | Ingredients | Content % (w/w) |
| 1 | Silver sulfadiazine | 1 |
| 2 | Chitosan | 0.25 |
| 3 | Lactic acid | 0.1 |
| 4 | White soft paraffin | 8.5 |
| 5 | Cetostearyl alcohol | 8.5 |
| 6 | Cetomacrogol 1000 | 2.5 |
| 7 | Methylparaben | 0.2 |
| 8 | Propylparaben | 0.02 |
| 9 | Light liquid paraffin | 5 |
| 10 | Propylene glycol | 10 |
| 11 | Disodium EDTA | 0.1 |
| 12 | Disodium hydrogen phosphate | 0.5 |
| 13 | Purified water | 63.50 |

EXPERIMENTAL EXAMPLE 1

Comparison of Strengths of Films Prepared According to the Examples of the Present Invention and Comparative Example 1

Each 0.5 g was taken from the formations according to Examples 1, 7 to 9, and 20 of the present invention and the cream formulation according to Comparative Example 1. Samples applied to 1.5 cm×1.5 cm PE plastic bag and dried at 37.5° C., thus forming films. The breaking strength of each film was measured using a texture analyzer (Stable Micro Systems, UK), and the results are shown in Table 7. It could be seen that the strengths of the films formed of the compositions of the present invention were significantly increased at least 10 times compared to Comparative Example 1.

TABLE 7

| | Breaking Strength of Film (N) |
|---|---|
| Comparative Example 1 | 1.3 |
| Example 1 | 78.7 |
| Example 7 | 13.8 |
| Example 8 | 22.1 |
| Example 9 | 46.8 |
| Example 20 | 14.1 |

EXPERIMENTAL EXAMPLE 2

Figure 1:
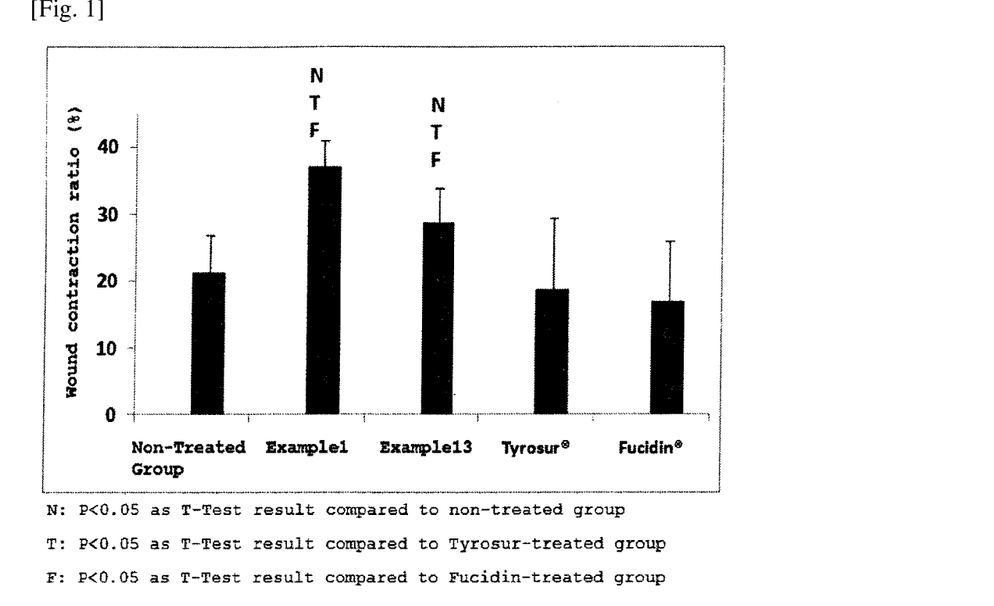
FIG. 1 shows the wound contraction ratio in abrasion animal models treated with Examples 1 and 13 and commercially available preparations such as Tyrosur® and Fucidin®.

Comparison of Wound Healing Effect of Compositions According to the Present Invention and Commercially Available Products in Abrasion Models SD rats with diabetes induced by intravenous injection of Streptozocin (40 mg/kg) were anesthetized and an abrasion with a diameter of 40 mm was created in each rat. The preparations of Examples 1 and 13 and commercially available Tyrosur® gel 1 (Engelhard Co., Ltd.) and Fucidin® ointment (DONG WHA Pharmaceutical Co., Ltd.) in Comparative Examples were used as the test materials. The experimental groups were divided into a non-treated group, a treated group of Example 1, a treatment group of Example 13, a Tyrosur gel-treated group, and a Fucidin ointment-treated group, and the treated groups were treated with 0.5 g of each test material once a day. The evaluation of wound healing was performed by calculating the wound contraction ratio, which represents the ratio of the initial wound size to the wound size after two days from the wound healing (Wound contraction ratio=(Initial wound size-Wound size after two days in each group)/Initial wound size×100(%)). The results are shown in FIG. 1. As can be seen from FIG. 1, the compositions of the present invention exhibited significant effects on the reduction in wound area (P<0.05) in the abrasion, compared to the non-treated group and the commercially available preparation such as Tyrosur gel and Fucidin ointment.

EXPERIMENTAL EXAMPLE 3

Figure 2:
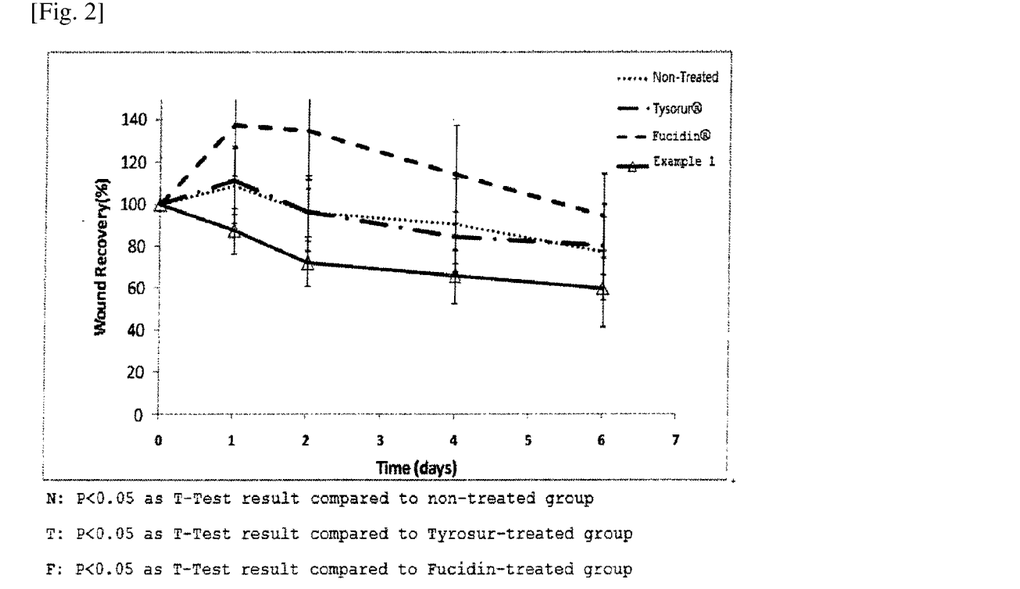
FIG. 2 shows the wound recovery rate in burned animal models treated with Example 1 and commercially available preparations such as Tyrosur® and Fucidin®.

Comparison of Wound Healing Effects of Compositions According to the Present Invention and Commercially Available Products in Burn Models SD rats were anesthetized and their back hair was removed. A burn wound was induced by contacting a cylindrical metal having a diameter of 1.5 cm and heated at 80° C. with the back of each rat. The epidermis of the wound was excised to the fascia. The preparations of Example 1 and commercially available Tyrosur® gel 1 (Engelhard) and Fucidin® ointment (DONG WHA Pharmaceutical Co., Ltd.) in Comparative Examples were used as the test materials. The experimental groups were divided into a non-treated group, a treated group of Example 1, a Tyrosur gel-treated group, and a Fucidin ointment-treated group, and the treated groups were treated with 0.5 g of each test material once a day. The evaluation of wound healing was performed by calculating the wound recovery rate, which represents the rate of wound recovery from the initial wound size after 1, 2, 4 and 6 days from the wound healing (Wound recovery rate=Wound size at 1, 2, 4 and 6 days in each group/Initial wound size×100(%)). The results are shown in FIG. 2. As can be seen from FIG. 2, the composition of the present invention exhibited a significant effect on the reduction in wound area (P<0.05) in the burn wound at 1, 2, 4 and 6 days from the wound healing, compared to the non-treated group and the commercially available preparation such as Tyrosur gel and Fucidin ointment.

The invention claimed is:

1. A pharmaceutical composition for wound healing, comprising:
    (a) a pharmaceutically active substance;
    (b) a chitosan or a salt thereof as a film-forming substance;
    (c) a solvent comprising water, at least one lower alcohol having 1 to 4 carbon atoms, or a mixture of water and at least one lower alcohol having 1 to 4 carbon atoms for dissolving the chitosan;
    (d) an acid for dissolving the chitosan; and
    (e) an additive selected from among a plasticizer, a thickener, a surfactant, a preservative, a flavoring agent, a stabilizer, a defoamer, an adhesive, a gellant, an emulsifier, an opacifier, a humectant, and mixtures thereof, wherein:
    the film-forming substance consists of the chitosan or a salt thereof;
    the film-forming substance is present in an amount of 0.4 to 10 wt % with respect to the total weight of the composition;
    the acid is selected from among lactic acid, acetic acid, citric acid, gluconic acid, malic acid, adipic acid, maleic acid, succinic acid, tartaric acid, and mixtures thereof;
    the additive is present in an amount of 0.1 to 10 wt % with respect to the total weight of the composition;
    a cream base component is not present in the composition; and
    the composition forms a film upon application to the skin and evaporation or volatilization of the solvent.

2. A method for treating a wound, comprising applying the pharmaceutical composition of claim 1 to a wound of a subject, wherein the pharmaceutical composition forms a film after application to protect the wound and improve wound healing.

3. The pharmaceutical composition of claim 1, wherein the acid is present in an amount of 0.2 to 20 wt % with respect to the total weight of the composition.

4. The pharmaceutical composition of claim 1, wherein the additive is a plasticizer and the plasticizer is selected from among propylene glycol, polyethylene glycol, propylene carbonate, PEG-8 caprylic/capric glycerides, 2-(2-ethoxyethoxy)ethanol, propylene glycol gicaprylate dicaprate, polyglyceryl-6 dioleate, propylene glycol laurate, propylene glycol caprylate, lauroyl, linoleoyl and oleoyl polyoxylglycerides, fractionated coconut oil, caprylic/capric triglycerides, glycerin and mixtures thereof and is present in an amount of 0.2 to 10 wt % with respect to the total weight of the composition.

5. The pharmaceutical composition of claim 1, wherein the additive is a thickener and the-thickener is selected from among hydroxypropyl cellulose, hydroxyethyl cellulose, xanthan gum, locust bean gum, arabic gum, guar gum, carbomer, polyethylene oxide, poloxamer and mixtures thereof and is present in an amount of 0.2 to 10 wt % with respect to the total weight of the composition.

6. The pharmaceutical composition of claim 1, wherein the additive is a surfactant and the surfactant is selected from among polysorbate, polyethylene hydroxystearate, polyethoxylated castor oil, ethylene oxide/propylene oxide copolymer, stearoyl macrogol-32 glycerides, lauroyl macrogol-32 glycerides, propylene glycol monocaprylate, caprylocaproyl macrogol-8 glycerides, sodium lauryl sulfate, sodium docusate, benzalkonium chloride, benzethonium chloride and mixtures thereof and is contained in an amount of 0.1 to 10 wt % with respect to the total weight of the composition.

7. The pharmaceutical composition of claim 1, wherein the pharmaceutically active substance comprises at least one selected from among an antibiotic, a wound healing accelerant, a disinfectant or sanitizer and a local anesthetic or anti-inflammatory agent.

8. The pharmaceutical composition of claim 7, wherein the pharmaceutically active substance comprises at least one selected from among tyrothricin, fusidic acid or a salt thereof, neomycin sulfate or a salt thereof, hydrocortisone, titrated extract of Centella asiatica, and combinations thereof.

9. The pharmaceutical composition of claim 1, wherein the composition is in the form of a gel, an ointment, or a liquid before application to a wound or to skin.

10. A pharmaceutical composition for wound healing, comprising:
    (a) a pharmaceutically active substance;
    (b) a chitosan or a salt thereof as a film-forming substance;
    (c) a solvent comprising water and at least one lower alcohol having 1 to 4 carbon atoms for dissolving the chitosan;
    (d) an acid for dissolving the chitosan;
    (e) a cream base component selected from among isopropyl palmitate, cetyl palmitate, paraffin, trioctanoin, soybean oil, sesame oil, olive oil, liver oil, oleic acid, stearic acid octyldodecanol, octyldodecyl myristate, a silicone compound, stearyl alcohol, stearyl glycyrrhetinate, polyoxyl stearate, squalane, cetostearyl alcohol, cetomacrogol, cetanol, sorbitan sesquioleate, petroleum jelly, white beeswax, yellow beeswax, myristyl alcohol, isopropyl myristate, sorbitan monooleate, sorbitan monostearate, glycerin monostearate, lecithin, hydrogenated castor oil, caprylic/capric triglyceride, lanolin, oleoyl macrogolglycerides, and mixtures thereof; and
    (f) an additive selected from among a plasticizer, a thickener, a surfactant, a preservative, a flavoring agent, a stabilizer, a defoamer, an analgesic agent, an antioxidant, an adhesive, a gellant, an emulsifier, an astringent, an opacifier, a humectant, and mixtures thereof, wherein:
    the film-forming substance consists of the chitosan or a salt thereof;

the film-forming substance is present in an amount of 0.4 to 10 wt % with respect to the total weight of the composition;

the acid is selected from among lactic acid, acetic acid, citric acid, gluconic acid, malic acid, adipic acid, maleic acid, succinic acid, tartaric acid, and mixtures thereof;

the additive is present in an amount of 0.1 to 30 wt % with respect to the total weight of the composition; and the composition forms a film upon application to the skin.

11. A pharmaceutical composition for wound healing, comprising:
(a) a pharmaceutically active substance;
(b) a chitosan or a salt thereof as the only film-forming substance;
(c) a solvent comprising water and at least one lower alcohol having 1 to 4 carbon atoms for dissolving the chitosan;
(d) an acid for dissolving the chitosan; and
(e) an additive selected from among a plasticizer, a thickener, a surfactant, a preservative, a flavoring agent, a stabilizer, a defoamer, an analgesic agent, an antioxidant, an adhesive, a gellant, an emulsifier, an astringent, an opacifier, a humectant, and mixtures thereof, wherein:

the film-forming substance is present in an amount of 0.4 to 10 wt % with respect to the total weight of the composition;

the acid is selected from among lactic acid, acetic acid, citric acid, gluconic acid, malic acid, adipic acid, maleic acid, succinic acid, tartaric acid, and mixtures thereof;

the additive is present in an amount of 0.1 to 30 wt % with respect to the total weight of the composition;

the composition does not contain a cream base component, or contains a cream base component and the weight ratio of the film-forming substance to the cream base component is 1 part or more film-forming substance to 50 parts or less of the cream base component; and the composition forms a film upon application to the skin and evaporation or volatilization of the solvent.

12. A pharmaceutical composition for wound healing, comprising:
(a) a pharmaceutically active substance;
(b) a chitosan or a salt thereof as a film-forming substance;
(c) a solvent comprising water and at least one lower alcohol having 1 to 4 carbon atoms for dissolving the chitosan;
(d) a cream base component;
(e) an acid for dissolving the chitosan; and
(f) an additive selected from among a plasticizer, a thickener, a surfactant, a preservative, a flavoring agent, a stabilizer, a defoamer, an analgesic agent, an antioxidant, an adhesive, a gellant, an emulsifier, an astringent, an opacifier, a humectant, and mixtures thereof, wherein:

the film-forming substance is present in an amount of 0.4 to 10 wt % with respect to the total weight of the composition;

the additive is present in an amount of 0.1 to 30 wt % with respect to the total weight of the composition;

the composition contains 1 part or more of the chitosan or a salt thereof to 50 parts or less of the cream base component; and the composition forms a film upon application to the skin and evaporation or volatilization of the solvent.

13. The pharmaceutical composition of claim 12, wherein:

the acid is selected from among lactic acid, acetic acid, citric acid, gluconic acid, malic acid, adipic acid, maleic acid, succinic acid, tartaric acid, and mixtures thereof; and the acid is present in an amount of 0.2 to 20 wt % with respect to the total weight of the composition.

14. The pharmaceutical composition of claim 12, wherein:

the plasticizer is selected from among propylene glycol, polyethylene glycol, propylene carbonate, PEG-8 caprylic/capric glycerides, 2-(2-ethoxyethoxy)ethanol, propylene glycol dicaprylate/dicaprate, polyglyceryl-6 dioleate, propylene glycol laurate, propylene glycol caprylate, lauroyl, linoleoyl and oleoyl polyoxylglycerides, fractionated coconut oil, caprylic/capric triglycerides, glycerin, and mixtures thereof; and the plasticizer is present in an amount of 0.2 to 10 wt % with respect to the total weight of the composition.

15. The pharmaceutical composition of claim 12, wherein:

the thickener is selected from among hydroxypropyl cellulose, hydroxyethyl cellulose, xanthan gum, locust bean gum, arabic gum, guar gum, carbomer, polyethylene oxide, poloxamer, and mixtures thereof; and the thickener is present in an amount of 0.2 to 10 wt % with respect to the total weight of the composition.

16. The pharmaceutical composition of claim 12, wherein:

the surfactant is selected from among polysorbate, polyethylene hydroxystearate, polyethoxylated castor oil, ethylene oxide/propylene oxide copolymer, stearoyl macrogol-32 glycerides, lauroyl macrogol-32 glycerides, propylene glycol monocaprylate, caprylocaproyl macrogol-8 glycerides, sodium lauryl sulfate, sodium docusate, benzalkonium chloride, benzethonium chloride, and mixtures thereof; and the surfactant is present contained in an amount of 0.1 to 10 wt % with respect to the total weight of the composition.

17. The pharmaceutical composition of claim 12, wherein:

the pharmaceutically active substance comprises at least one selected from among an antibiotic, a wound healing accelerant, a disinfectant or sanitizer and a local anesthetic or anti-inflammatory agent; or the pharmaceutically active substance comprises at least one selected from among tyrothricin, fusidic acid or a salt thereof, neomycin sulfate or a salt thereof, hydrocortisone, titrated extract of Centella asiatica and combinations thereof.

* * * * *

UNITED STATES PATENT AND TRADEMARK OFFICE
CERTIFICATE OF CORRECTION

PATENT NO. : 10,278,928 B2
APPLICATION NO. : 14/765318
DATED : May 7, 2019
INVENTOR(S) : Kim et al.

It is certified that error appears in the above-identified patent and that said Letters Patent is hereby corrected as shown below:

In the Claims

At Column 17, Line 62, to Column 18, Line 5, please replace Claim 4 with the following amended claim:
4. The pharmaceutical composition of claim 1, wherein:
    the additive is a plasticizer and the plasticizer is selected from among propylene glycol, polyethylene glycol, propylene carbonate, PEG-8 caprylic/capric glycerides, 2-(2-ethoxyethoxy)ethanol, propylene glycol dicaprylate/dicaprate, polyglyceryl-6 dioleate, propylene glycol laurate, propylene glycol caprylate, lauroyl, linoleoyl and oleoyl polyoxylglycerides, fractionated coconut oil, caprylic/capric triglycerides, glycerin, and mixtures thereof; and
    the plasticizer is present in an amount of 0.2 to 10 wt % with respect to the total weight of the composition.

At Column 18, Lines 6-12, please replace Claim 5 with the following amended claim:
5. The pharmaceutical composition of claim 1, wherein:
    the additive is a thickener and the thickener is selected from among hydroxypropyl cellulose, hydroxyethyl cellulose, xanthan gum, locust bean gum, arabic gum, guar gum, carbomer, polyethylene oxide, poloxamer, and mixtures thereof; and
    the thickener is present in an amount of 0.2 to 10 wt % with respect to the total weight of the composition.

At Column 18, Lines 13-23, please replace Claim 6 with the following amended claim:
6. The pharmaceutical composition of claim 1, wherein:
    the additive is a surfactant and the surfactant is selected from among polysorbate, polyethylene hydroxystearate, polyethoxylated castor oil, ethylene oxide/propylene oxide copolymer, stearoyl macrogol-32 glycerides, lauroyl macrogol-32 glycerides, propylene glycol monocaprylate, caprylocaproyl macrogol-8 glycerides, sodium lauryl sulfate, sodium docusate, benzalkonium chloride, benzethonium chloride, and mixtures thereof; and Signed and Sealed this
Eighteenth Day of June, 2019

Andrei Iancu
*Director of the United States Patent and Trademark Office* the surfactant is present in an amount of 0.1 to 10 wt % with respect to the total weight of the composition.

At Column 20, Lines 37-49, please replace Claim 16 with the following amended claim:
16. The pharmaceutical composition of claim 12, wherein:
    the surfactant is selected from among polysorbate, polyethylene hydroxystearate, polyethoxylated castor oil, ethylene oxide/propylene oxide copolymer, stearoyl macrogol-32 glycerides, lauroyl macrogol-32 glycerides, propylene glycol monocaprylate, caprylocaproyl macrogol-8 glycerides, sodium lauryl sulfate, sodium docusate, benzalkonium chloride, benzethonium chloride, and mixtures thereof; and
    the surfactant is present in an amount of 0.1 to 10 wt % with respect to the total weight of the composition.

At Column 20, Lines 50-61, please replace Claim 17 with the following amended claim:
17. The pharmaceutical composition of claim 12, wherein:
    the pharmaceutically active substance comprises at least one selected from among an antibiotic, a wound healing accelerant, a disinfectant or sanitizer and a local anesthetic or anti-inflammatory agent; or
    the pharmaceutically active substance comprises at least one selected from among tyrothricin, fusidic acid or a salt thereof, neomycin sulfate or a salt thereof, hydrocortisone, titrated extract of Centella asiatica, and combinations thereof.